(12) United States Patent
Schmotzer

(10) Patent No.: US 8,185,458 B2
(45) Date of Patent: May 22, 2012

(54) OCCUPATIONAL THERAPY AND ERGONOMIC SYSTEM

(76) Inventor: Theresa M. Schmotzer, Avondale, AZ (US)

( * ) Notice: Subject to any disclaimer, the term of this patent is extended or adjusted under 35 U.S.C. 154(b) by 973 days.

(21) Appl. No.: 11/948,252

(22) Filed: Nov. 30, 2007

(65) Prior Publication Data

US 2008/0133297 A1 Jun. 5, 2008

Related U.S. Application Data

(60) Provisional application No. 60/868,040, filed on Nov. 30, 2006.

(51) Int. Cl.
*G06Q 40/00* (2012.01)
(52) U.S. Cl. ............................................. 705/35; 705/37
(58) Field of Classification Search .................... 705/35, 705/37
See application file for complete search history.

(56) References Cited

U.S. PATENT DOCUMENTS

| | | | | |
|---|---|---|---|---|
| 5,583,758 | A * | 12/1996 | McIlroy et al. | 705/2 |
| 7,113,940 | B1 * | 9/2006 | Jensen | 1/1 |
| 2003/0149596 | A1 * | 8/2003 | Bost | 705/2 |
| 2003/0154098 | A1 * | 8/2003 | Kalnas et al. | 705/1 |
| 2004/0249701 | A1 * | 12/2004 | Schwarz | 705/11 |
| 2005/0261957 | A1 * | 11/2005 | Fisher et al. | 705/11 |
| 2008/0120139 | A1 * | 5/2008 | Banks | 705/3 |

* cited by examiner

*Primary Examiner* — Thomas Dixon
*Assistant Examiner* — Benjamin S Fields
(74) *Attorney, Agent, or Firm* — Sand & Sebolt

(57) ABSTRACT

A system for preventing on the job injuries comprising identifying a company which will benefit from the system and approaching the same with a business proposal. Once hired, a therapist evaluates the company's workplace environment and an initial physical state of a group of employees employed by the company; assesses data gathered during the evaluation; develops a corrective therapeutic program to address areas of concern identified during the assessment; implements the corrective therapeutic through instruction of the employees; and conducts periodic follow-up evaluations, adjusting the corrective therapeutic program as required until the outcomes of the system are achieved.

32 Claims, 30 Drawing Sheets

FIG - 3 (page 1/7)

STARStretch™ Discomfort Questionnaire: Baseline

Please indicate if you currently have discomfort at work. In addition to pain and soreness, this may include numbness, tingling, or weakness.

Please use blue or black ink and fill in circles like this ●, not like this ✗ ⊘ ⊖

| Location | Employee ID | Today's Date |
|---|---|---|

Pay Location — Work ZIP Code — Use Last 4 Digits SS# — M M D D Y Y

0 O O O   O O O O O 0    0 O O O O    0 O O O O O O 0
1 O O O   O O O O O 1    1 O O O O    1 O O O O O O 1
2 O O O   O O O O O 2    2 O O O O    2   O O O O O 2
3 O O O   O O O O O 3    3 O O O O    3 O O O O O 3
4 O O O   O O O O O 4    4 O O O O    4 O   O O O 4
5 O O O   O O O O O 5    5 O O O O    5 O   O O O 5
6 O O O   O O O O O 6    6 O O O O    6 O   O O O 6
7 O O O   O O O O O 7    7 O O O O    7 O   O O O 7
8 O O O   O O O O O 8    8 O O O O    8 O   O O O 8
9 O O O   O O O O O 9    9 O O O O    9 O   O O O 9

O Plant    O Customer Service Office    ← Be sure you pick one!

Discomfort Information

| Area | Pain Level | | | | Frequency | | | |
|---|---|---|---|---|---|---|---|---|
| | None | Mild | Moderate | Severe | Never | About Half the Time | | Constant |
| | 0 1 2 3 4 5 6 7 8 9 10 | | | | 0 1 2 3 4 5 6 7 8 9 10 | | | |
| Neck – Shoulders – Upper back | O O O O O O O O O O O | | | | O O O O O O O O O O O | | | |
| Wrist – Hands – Arms | O O O O O O O O O O O | | | | O O O O O O O O O O O | | | |
| Lower Back – Legs | O O O O O O O O O O O | | | | O O O O O O O O O O O | | | |
| Feet or Other Area | O O O O O O O O O O O | | | | O O O O O O O O O O O | | | |
| | 0 1 2 3 4 5 6 7 8 9 10 | | | | 0 1 2 3 4 5 6 7 8 9 10 | | | |

Name: _____
(Last, First) Please Print Clearly

Comments: _____

CONFIDENTIAL

REMEDY  PACIFIC  JOB DESCRIPTION: _____
LICENSED OCCUPATIONAL      TIME: _____
PROFESSIONAL ERGONOMIC     THERAPIST: _____
HEALTH SERVICES            DATE: _____
Job Title(s) Observed: (List)
[ ]
Reported Difficulties: (List)
[ ]
Ergonomic Factors: (List)
[ ]
Recommendations: (List)
[ ]
Contextual Barriers: (List)
[ ]
FIG - 3 (page 2/7)

FIG - 3 (page 3/7)

REMEDY PACIFIC
LICENSED OCCUPATIONAL
PROFESSIONAL ERGONOMIC
HEALTH SERVICES

JOB DESCRIPTION: _____
TIME: _____
THERAPIST: _____
DATE: _____

| EVALUATION | YES/NO | % of frequency of task |
|---|---|---|
| Are actions performed with sudden or jerking movement? | | |
| Are tasks performed in an unbalanced and/or uncomfortable position? | | |
| Is there repetitive bending, twisting, or overreaching? | | |
| Is a load shared unevenly between both hands, or lifted by one hand? | | |
| Does the task require a full range of joint movement which is prolonged or repetitive? | | |
| Is there a need to bend over to one side to lift or move an object? | | |
| Is an object pushed or pulled across the front of the body? | | |
| Is the employee facing the task? | | |
| Is the task within eye level? | | |
| Is the majority of the task within easy reach? | | |
| Does the layout fit the employee? | | |
| Does the work height fit the employee? | | |
| Is there adequate foot space? | | |
| Is there repetitive reaching above shoulder? | | |
| Is the employee bending knees and keeping ears over shoulders when reaching below waist? | | |
| Is the employee pivoting on feet? | | |
| Is the same task being performed repetitively? | | |
| Are loads being moved correctly? | | |
| Are the shoulders tucked into side when pushing or pulling? | | |
| Are the knees bent with ears over shoulders when lifting? | | |
| Are items being carried at waist level? | | |
| Does the employee wear gloves? | | |
| Do they fit snugly to hand? | | |
| Are employees practicing safe work methods? | | |
| Are there a sufficient number of employees to meet the deadline? (Ask SDO) | | |
| Is there a good team effort? | | |
| Do the employees help one another with heavy lifting? | | |
| Are broken items red tagged? | | |
| Is the work flow affected by poor design or delays from another operation? | | |
| Is vibration a factor? | | |
| Are there supportive mats? | | |
| Are there pressure points, if so, where? | | |
| Is there prolonged-- O standing -- O sitting? (Fill in bubble) | | |

FIG - 3 (page 4/7)

REMEDY PACIFIC
LICENSED OCCUPATIONAL
PROFESSIONAL ERGONOMIC
HEALTH SERVICES

JOB DESCRIPTION: _____
TIME: _____
THERAPIST: _____
DATE: _____

WHICH MUSCLE GROUPS ARE BEING OVERUSED

| SPINAL DYSFUNCTION | |
|---|---|
| Lordosis (Backward Bending) | |
| Scoliosis (Crookedness) | |
| Kyposis (Humpback) | |

| ATLANTO-AXIAL JOINTS | Observations |
|---|---|
| Rotation (Obliquus Capitis Inferior, Rectus Capitis Posterior, Longissimus Capitis, Splenius Capitis, Sternocleidomastoid, Rectus Capitis Posterior) | |
| Flexion (Obliquus Capitis Inferior,) | |
| Extension (Iliocostalis, Longissimus, Longissimus Capitis, Spinalis, Semispinalis Cervicis, Semispinalis Capitis) | |
| SPINE | |
| Flexion (Multifidus) | |
| Extension (Semispinalis, Interspinales, Intertransversarii, Levator Costarum, Spinalis Thoracis, | |
| Lateral Rotation (Multifidus, Rotatores, Semispinalis) | |

| SHOULDER | | Goniometer Measurements | |
|---|---|---|---|
| | | Typical | End Pt. |
| Shoulder Flexors (Ant. Delts, Coracobrachialis, Pectoralis-Major, Biceps) | 0-180 | | |
| Shoulder Extensors (Latissimus dorsi, Teres Major, Post. Delts., Triceps) | 0-60 | | |
| Shoulder Adductors (Latissimus dorsi, Teres Major, Pectoralis) | | | |
| Shoulder Abductors (Supraspinatus, Middle Deltoid) | 0-180 | | |
| External Rotators (Infraspinatus, Teres Minor, Posterior Deltoid) | 0-60 | | |
| Internal Rotators (Supscap. Teres Major, Latissimus Dorsi, Pectoralis, Ant Delt.) | 0-80 | | |
| SCAPULA | | | |
| Elevation (Upper Trapezius, Levator Scapulae) | No Norm | | |
| Depression (Lower Trapezius, Latissimus Dorsi) | No Norm | | |
| Adduction (Middle Trapezius, Rhomboid) | No Norm | | |
| Abduction (Serratus Anterior) | No Norm | | |
| ELBOW & FOREARM | | | |
| Flexion (Biceps, Brachioradialis, Brachialis) | 0-150 | | |
| Extension (Triceps) | 0-150 | | |
| Supination (Supinator, Biceps) | 0-90 | | |
| Pronation (Pronator Teres, Pronator Quadratus) | 0-90 | | |
| WRIST | | | |
| Flexion (Flexor Carpi Radialis Longus, Brevis, & Ulnaris) | 0-80 | | |
| Extension (Ext. Carpi Radialis, Longus & Brevis, Ext. Carpi Ulnaris) | 0-70 | | |
| Ulnar Deviation (Ext. Carpi Ulnaris, Flexor Carpi Ulnaris) | 0-30 | | |
| Radial Deviation (Flexor Carpi Radialis, Ext. Carpi Radialis) | 0-20 | | |

REMEDY  PACIFIC
LICENSED OCCUPATIONAL
PROFESSIONAL ERGONOMIC
HEALTH SERVICES

JOB DESCRIPTION: _____
TIME: _____
THERAPIST: _____
DATE: _____

| THUMB | | Goniometer Measurements | |
|---|---|---|---|
| | | Typical | End Pt. |
| CMC Flexion (Flexor Pollicis Longus & Brevis) | 0-15 | | |
| CMC Extension (Extensor Pollicis Longus & Brevis) | 0-20 | | |
| MP Flexion-Extension (Extensor Digitorum, Pollicis Longus & Brevis) | 0-50 | | |
| IP Flexion-Extension (Lumrical) | 0-80 | | |
| Abduction (Abductor Pollicis) | cm. | | |
| Opposition (Opponens Pollicis & Digiti Minimi) | cm. | | |
| CMC Flexion (Flexor Pollicis Longus & Brevis) | 0-15 | | |
| INDEX FINGER | | | |
| MP Flexion-Extension (Extensor Digitorum) | 0-90 | | |
| PIP Flexion-Extension (Flexor Superficialis) | 0-100 | | |
| DIP Flexion-Extension (Flexor Profundus) | 0-90 | | |
| IP (Lumrical) | | | |
| Abduction (Dorsal Interosseus) | No Norm | | |
| Adduction (Palmar Interosseus) | No Norm | | |
| MIDDLE FINGER | | | |
| MP Flexion-Extension (Extensor Digitorum) | 0-90 | | |
| PIP Flexion-Extension (Flexor Superficialis) | 0-100 | | |
| DIP Flexion-Extension (Flexor Profundus) | 0-90 | | |
| IP (Lumrical) | | | |
| Abduction (Dorsal Interosseus) | No Norm | | |
| Adduction (Palmar Interosseus) | No Norm | | |
| RING FINGER | | | |
| MP Flexion-Extension (Extensor Digitorum) | 0-90 | | |
| PIP Flexion-Extension (Flexor Superficialis) | 0-100 | | |
| DIP Flexion-Extension (Flexor Profundus) | 0-90 | | |
| IP (Lumrical) | | | |
| Abduction (Dorsal Interosseus) | No Norm | | |
| Adduction (Palmar Interosseus) | No Norm | | |
| LITTLE FINGER | | | |
| MP Flexion-Extension (Extensor Digitorum) | 0-90 | | |
| PIP Flexion-Extension (Flexor Digiti Minimi) | 0-100 | | |
| DIP Flexion-Extension (Flexor Profundus) | 0-90 | | |
| IP (Lumrical) | | | |
| Abduction (Dorsal Interosseus, Abductor Digiti Minimi) | No Norm | | |
| Adduction (Adductor Digiti Minimi) | No Norm | | |

FIG - 3 (page 5/7)

REMEDY PACIFIC
LICENSED OCCUPATIONAL
PROFESSIONAL ERGONOMIC
HEALTH SERVICES

JOB DESCRIPTION: _____
TIME: _____
THERAPIST: _____
DATE: _____

| HIP | | Goniometer Measurements | |
|---|---|---|---|
| | | Typical | End Pt. |
| Flexion (Iliopsoas, Illiacus, Sartorius) | 0-125 | | |
| Extension (Gluteus Maximus, Sartorius, Semitendinosus, Semimembranosus, Biceps Femoris) | 0-115 | | |
| Abduction ([TFL], Sartorius, Gluteus Medius & Minimus) | 0-45 | | |
| Adduction (Pectineus, Gracilis, Adductor Longus, Brevis, & Magnus) | 45-0 | | |
| Lateral Rotation (Obturator Externus & Internus, Gemelli Superior & Inferior, Quadratus Femoris, Semitendinosus, Semimembranosus) | 0-45 | | |
| Medial Rotation (Gluteus Medius & Minimus, Gracilis) | 0-45 | | |
| KNEE | | | |
| Flexion (Hamstrings, Biceps Femoris, Semitendinosus, Semimembranosus, Gastrocnemius, Popliteus) | 0-135 | | |
| Ext. (Quad. & Rectus Femoris, Vastus Lateralis, Medialis, & Intermedius, TFL) | 120-0 | | |
| ANKLE | | | |
| Dorsiflexion (Tibialis Ant., Ext. Digitorum Longus, Ext. Hallucis Longus) | 0-20 | | |
| Plantar Flexion (Soleus) | 0-50 | | |
| FOOT | | | |
| Dorsiflexion w/knee flexed (Flexor Digtorum Longus & Brevis) | 0-15 | | |
| Dorsiflexion w/knee extended | 0-10 | | |
| Hallux dorsiflexion (Flexor Hallucis Longus [FHL] & Brevis) | 0-60 | | |
| Extension (Extensor Digitorum) | 0-40 | | |
| Plantarflexion (Gastrocnemius, Soleus, Plantaris, FHL, Tibialis Posterior) | 0-25 | | |
| Inversion | 0-35 | | |
| Eversion | 0-25 | | |

FIG - 3 (page 6/7)

REMEDY  PACIFIC
LICENSED OCCUPATIONAL
PROFESSIONAL ERGONOMIC
HEALTH SERVICES

JOB DESCRIPTION: _____
TIME: _____
THERAPIST: _____
DATE: _____

RISK ANALYSIS SUMMARY

Recommended Interventions (Check all that apply)

| | | | |
|---|---|---|---|
| ☐ | Work Methods Instruction/Training | ☐ | Body Mechanics Instruction/Training |
| ☐ | Work Stretches | ☐ | Home Stretches |
| ☐ | Work-Related Strengthening | ☐ | Posture Education/Training |
| ☐ | Job Rotation/Modification (If available) | ☐ | Train-the-Trainer Program |

Equipment Recommendations (To be determined in conjunction with Company Safety Department)*

| Equipment | Source(s) | Cost* |
|---|---|---|
| | | |
| | | |
| | | |

*Will be determined following approval by Company

_____   _____   _____
Therapist Signature   Telephone Number   Date

The data in this volume shall not be disclosed outside the USPS and shall not be duplicated, used, or disclosed in whole or in part for any purpose other than to evaluate the proposal. If a contract is awarded to this offer or as a result of or in connection with the submission of these data, the USPS shall have the right to duplicate, use, or disclose the data to the extent provided in this contract.

FIG - 3 (page 7/7)

FIG - 4 (page 1/7)

Discomfort Questionnaire: Baseline

Please indicate if you currently have discomfort at work. In addition to pain and soreness, this may include numbness, tingling, or weakness.

Please use blue or black ink and fill in circles like this ●, not like this ✗ ✓ ⊘

Location

| Pay Location | Work ZIP Code |
|---|---|
| 3 1 7 | 9 2 8 9 9 |

Pay Location digits: 3 (filled at row 3, col 1), 1 (row 1, col 2), 7 (row 7, col 3)

Work ZIP Code digits: 9, 2, 8, 9, 9

● Plant    O Customer Service Office

Employee ID

Use Last 4 Digits SS#: 3 8 2 4

Today's Date

M M D D Y Y : 0 6 2 0 0 6

← Be sure you pick one!

Discomfort Information

| Area | Pain Level (None 0 – Severe 10) | Frequency (Never 0 – Constant 10) |
|---|---|---|
| Neck – Shoulders – Upper back | 8 | 9 |
| Wrist – Hands – Arms | 1 | 1 |
| Lower Back – Legs | 10 | 6 |
| Feet or Other Area | 2 | 2 |

Name: _____ (Last, First) Please Print Clearly

Comments: work injury @ right shoulder (chronic) Left leg started hurting worse day by day

CONFIDENTIAL

REMEDY  PACIFIC  JOB DESCRIPTION: Automation
LICENSED OCCUPATIONAL  TIME: Tour III
PROFESSIONAL ERGONOMIC  THERAPIST: ___
HEALTH SERVICES  DATE: January 22, 2006

Job Title(s) Observed: (List)

| Automation |
|---|

Reported Difficulties: (List)

| Height of shelves on the machine.<br>Height of shelves on the tray rack.<br>Tray rack trays jamming.<br>Old anti-fatigue mat. |
|---|

Ergonomic Factors: (List)

| Repetitive reaching loading letters.<br>Repetitive twisting to load bread cart.<br>Repetitive grasping handfuls of letters.<br>Repetitive reaching to pull down letters.<br>Repetitive de-sleaving trays.<br>Repetitive bending and twisting.<br>Pull out shelves on bread cart.<br>Bending and to load tray rack. |
|---|

FIG - 4 (page 2/7)

Recommendations: (List)

| Load letters pivoting on feet.<br>Stoop or bend knees while pulling down letters to keep from bending back.<br>Keep wrist straight while you are working focus on using larger joints.<br>Grasp smaller bundles.<br>Minimize vibration levels. |
|---|

Contextual Barriers: (List)

| Vibrates.<br>Height to load trays.<br>Worn out anti-fatigue mat.<br>Step is difficult to pull down. |
|---|

REMEDY  PACIFIC  
LICENSED OCCUPATIONAL  
PROFESSIONAL ERGONOMIC  
HEALTH SERVICES JOB DESCRIPTION: Automation  
TIME: Tour III  
THERAPIST: _____  
DATE: January 22, 2006

| EVALUATION | YES/NO | % of frequency of task |
|---|---|---|
| Are actions performed with sudden or jerking movement? | Y | 20 |
| Are tasks performed in an unbalanced and/or uncomfortable position? | Y | 80 |
| Is there repetitive bending, twisting, or overreaching? | Y | 50 |
| Is the work all ● static or ○ dynamic? (Fill in bubble) | Y | 30 |
| Is a load shared unevenly between both hands, or lifted by one hand? | Y | 30 |
| Does the task require a full range of joint movement which is prolonged or repetitive? | Y | 20 |
| Is there a need to bend over to one side to lift or move an object? | Y | 50 |
| Is an object pushed or pulled across the front of the body? | Y | 80 |
| Is the employee facing the task? | Y | 50 |
| Is the task within eye level? | Y | 30 |
| Is the majority of the task within easy reach? | Y | 20 |
| Does the layout fit the employee? | Y | 50 |
| Does the work height fit the employee? | Y | 50 |
| Is there adequate foot space? | Y | 100 |
| Repetitive reaching above shoulder? | Y | 20 |
| Is the employee bending knees keeping ears over shoulders when reaching below waist? | Y | 30 |
| Repetitive reaching below waist? | Y | 30 |
| Is the employee pivoting on feet? | Y | 30 |
| Is the same task being performed repetitively? | Y | 80 |
| Are loads being moved correctly? | Y | 30 |
| Shoulders tucked into side when pushing or pulling? | Y | 30 |
| Knees bent with ears over shoulders when lifting? | Y | 50 |
| Carrying items at waist level? | Y | 80 |
| Does the employee wear gloves? | Y | 90 |
| Do they fit snugly to hand? | Y | 90 |
| Are employees practicing safe work methods? | Y | 70 |
| Are there a sufficient number of employees to meet the deadline? Ask ____? | Y | 60 |
| Is there a good team effort? | Y | 80 |
| Do employees help one another with heavy lifting? | Y | 80 |
| Are broken items red tagged? | Y | 100 |
| Is the work task within ergonomic ranges? | Y | 60 |
| Are there pressure points? | N | 100 |
| Are hand tools designed ergonomically? | Y | 80 |
| Is the work flow affected by poor design or delays from another operation? | Y | 20 |

FIG - 4 (page 3/7)

REMEDY  PACIFIC
LICENSED OCCUPATIONAL
PROFESSIONAL ERGONOMIC
HEALTH SERVICES JOB DESCRIPTION: Automation
TIME: Tour III
THERAPIST: _____
DATE: January 22, 2006

| | | |
|---|---|---|
| Is there overtime? | Y | 80 |
| Is vibration a factor? | Y | 60 |
| Are there supportive mats? | Y | 100 |
| Pressure points, where? | N | 100 |
| Prolonged-- ● standing -- O sitting? (Fill in bubble) | Y | 100 |
| Is O heat or O cold a factor? (Fill in bubble) | N | 100 |
| Does this person have days off? | Y | 1/7 |

Which muscle groups are being overused?

| SPINAL DYSFUNCTION | |
|---|---|
| Lordosis (Backward Bending) | No |
| Scoliosis (Crookedness) | No |
| Kyposis (Humpback) | No |

| ATLANTO-AXIAL JOINTS | Observations |
|---|---|
| Rotation (Obliquus Capitis Inferior, Rectus Capitis Posterior, Longissimus Capitis, Splenius Capitis, Sternocleidomastoid, Rectus Capitis Posterior) | 50% |
| Flexion (Obliquus Capitis Inferior, | 80% |
| Extension (Iliocostalis, Longissimus, Longissimus Capitis, Spinalis, Semispinalis Cervicis, Semispinalis Capitis) | 0% |
| SPINE | |
| Flexion (Multifidus) | 40% |
| Extension (Semispinalis, Interspinales, Intertransversarii, Levator Costarum, Spinalis Thoracis, | 0% |
| Lateral Rotation (Multifidus, Rotatores, Semispinalis) | 60% |
| SHOULDER | Goniometer Measurements |
| Shoulder Flexors (Ant. Delts, Coracobrachialis, Pectoralis-Major, Biceps) 0-180 | 120 |
| Shoulder Extensors (Latissimus dorsi, Teres Major, Post. Delts., Triceps) 0-60 | 0 |
| Shoulder Adductors (Latissimus dorsi, Teres Major, Pectoralis) | 0 |
| Shoulder Abductors (Supraspinatus, Middle Deltoid) 0-180 | 110 |
| External Rotators (Infraspinatus, Teres Minor, Posterior Deltoid) 0-60 | 60 |
| Internal Rotators (Supscap. Teres Major, Latissimus Dorsi, Pectoralis, Ant Delt.) 0-80 | 60 |
| SCAPULA | |
| Elevation (Upper Trapezius, Levator Scapulae) | No Norm | 60% |
| Depression (Lower Trapezius, Latissimus Dorsi) | No Norm | 0 |
| Adduction (Middle Trapezius, Rhomboid) | No Norm | 0 |
| Abduction (Serratus Anterior) | No Norm | 20% |
| ELBOW & FOREARM | |
| Flexion (Biceps, Brachioradialis, Brachialis) | 0-150 | 90 |
| Extension (Triceps) | 0-150 | 0 |

FIG - 4 (page 4/7)

REMEDY  PACIFIC　　JOB DESCRIPTION: <u>Automation</u>
LICENSED OCCUPATIONAL　TIME: <u>Tour III</u>
PROFESSIONAL ERGONOMIC　THERAPIST: _____
HEALTH SERVICES　　DATE: <u>January 22, 2006</u>

| | | |
|---|---|---|
| Supination (Supinator, Biceps) | 0-90 | 45 but resistive |
| Pronation (Pronator Teres, Pronator Quadratus) | 0-90 | 45 |
| WRIST | | |
| Flexion (Flexor Carpi Radialis Longus, Brevis, & Ulnaris) | 0-80 | 80 |
| Extension (Ext. Carpi Radialis, Longus & Brevis, Ext. Carpi Ulnaris) | 0-70 | 70 |
| Ulnar Deviation (Ext. Carpi Ulnaris, Flexor Carpi Ulnaris) | 0-30 | 30 |
| Radial Deviation (Flexor Carpi Radialis, Ext. Carpi Radialis) | 0-20 | 15 |
| THUMB | | Goniometer Measurements |
| CMC Flexion (Flexor Pollicis Longus & Brevis) | 0-15 | 15 |
| CMC Extension (Extensor Pollicis Longus & Brevis) | 0-20 | 0 |
| MP Flexion-Extension (Extensor Digitorum, Pollicis Longus & Brevis) | 0-50 | 50 |
| IP Flexion-Extension (Lumrical) | 0-80 | 40 |
| Abduction (Abductor Pollicis) | cm. | |
| Opposition (Opponens Pollicis & Digiti Minimi) | cm. | |
| CMC Flexion (Flexor Pollicis Longus & Brevis) | 0-15 | 5 |
| INDEX FINGER | | |
| MP Flexion-Extension (Extensor Digitorum) | 0-90 | 50 |
| PIP Flexion-Extension (Flexor Superficialis) | 0-100 | 50 |
| DIP Flexion-Extension (Flexor Profundus) | 0-90 | 20 |
| IP (Lumrical) | | |
| Abduction (Dorsal Interosseus) | No Norm | |
| Adduction (Palmar Interosseus) | No Norm | |
| MIDDLE FINGER | | |
| MP Flexion-Extension (Extensor Digitorum) | 0-90 | 50 |
| PIP Flexion-Extension (Flexor Superficialis) | 0-100 | 50 |
| DIP Flexion-Extension (Flexor Profundus) | 0-90 | 20 |
| IP (Lumrical) | | |
| Abduction (Dorsal Interosseus) | No Norm | |
| Adduction (Palmar Interosseus) | No Norm | |
| RING FINGER | | |
| MP Flexion-Extension (Extensor Digitorum) | 0-90 | 50 |
| PIP Flexion-Extension (Flexor Superficialis) | 0-100 | 50 |
| DIP Flexion-Extension (Flexor Profundus) | 0-90 | 20 |
| IP (Lumrical) | | |
| Abduction (Dorsal Interosseus) | No Norm | |
| Adduction (Palmar Interosseus) | No Norm | |
| LITTLE FINGER | | |
| MP Flexion-Extension (Extensor Digitorum) | 0-90 | 50 |
| PIP Flexion-Extension (Flexor Digiti Minimi) | 0-100 | 50 |
| DIP Flexion-Extension (Flexor Profundus) | 0-90 | 20 |

FIG - 4 (page 5/7)

REMEDY  PACIFIC  LICENSED OCCUPATIONAL  PROFESSIONAL ERGONOMIC  HEALTH SERVICES JOB DESCRIPTION: <u>Automation</u>  
TIME: <u>Tour III</u>  
THERAPIST: _____  
DATE: <u>January 22, 2006</u>

| IP (Lumrical) | | |
|---|---|---|
| Abduction (Dorsal Interosseus, Abductor Digiti Minimi) | No Norm | |
| Adduction (Adductor Digiti Minimi) | No Norm | |

| HIP | | Goniometer Measurements |
|---|---|---|
| Flexion (Iliopsoas, Illiacus, Sartorius) | 0-125 | 125 |
| Extension (Gluteus Maximus, Sartorius, Semitendinosus, Semimembranosus, Biceps Femoris ) | 0-115 | 0 |
| Abduction ( [TFL] , Sartorius, Gluteus Medius & Minimus) | 0-45 | 20 |
| Adduction (Pectineus, Gracilis, Adductor Longus, Brevis, & Magnus) | 45-0 | 0 |
| Lateral Rotation (Obturator Externus & Internus, Gemelli Superior & Inferior, Quadratus Femoris, Semitendinosus, Semimembranosus) | 0-45 | 20 |
| Medial Rotation (Gluteus Medius & Minimus, Gracilis) | 0-45 | 0 |
| KNEE | | |
| Flexion (Hamstrings, Biceps Femoris, Semitendinosus, Semimembranosus, Gastrocnemius, Popliteus) | 0-135 | 90 |
| Ext. (Quad. & Rectus Femoris, Vastus Lateralis, Medialis, & Intermedius, TFL) | 120-0 | 0 |
| ANKLE | | |
| Dorsiflexion (Tibialis Ant., Ext. Digitorum Longus, Ext. Hallucis Longus) | 0-20 | 20 |
| Plantar Flexion (Soleus) | 0-50 | 20 |
| FOOT | | |
| Dorsiflexion w/knee flexed (Flexor Digtorum Longus & Brevis) | 0-15 | 15 |
| Dorsiflexion w/knee extended | 0-10 | 0 |
| Hallux dorsiflexion (Flexor Hallucis Longus [FHL] & Brevis) | 0-60 | 20 |
| Extension (Extensor Digitorum) | 0-40 | 0 |
| Plantarflexion (Gastrocnemius, Soleus, Plantaris, FHL, Tibialis Posterior) | 0-25 | 10 |
| Inversion | 0-35 | 0 |
| Eversion | 0-25 | 10 |

FIG - 4 (page 6/7)

REMEDY  PACIFIC
LICENSED OCCUPATIONAL
PROFESSIONAL ERGONOMIC
HEALTH SERVICES JOB DESCRIPTION: <u>Automation</u>
TIME: <u>Tour III</u>
THERAPIST: _____
DATE: <u>January 22, 2006</u>

RISK ANALYSIS SUMMARY

<u>Recommended Interventions</u> (Check all that apply)

| | | | |
|---|---|---|---|
| √ | Work Methods Instruction/Training | √ | Body Mechanics Instruction/Training |
| √ | Work Stretches | | Home Stretches |
| √ | Work-Related Strengthening | | Posture Education/Training |
| √ | Job Rotation/Modification (If available) | √ | Train-the-Trainer Program |

<u>Equipment Recommendations</u> (To be determined in conjunction with Company Safety Department)*

| Equipment | Source(s) | Cost* |
|---|---|---|
| anti-fatigue mats | Catalog | TBD |
| | | |
| | | |

*Will be determined following approval by Company

FIG - 4 (page 7/7)

FIG. 5

| Opt Out | Last Name | First Name | P/L | Date | PAIN (Neck) | FREQ (Neck) | PAIN (Wrist) | FREQ (Wrist) | PAIN (Back) | FREQ (Back) | PAIN (Feet) | FREQ (Feet) | WHT Date | EI Date | Therapist |
|---|---|---|---|---|---|---|---|---|---|---|---|---|---|---|---|
| | Individual 1 | | 133 | 8/12/2006 | 3 | 3 | 7 | 6 | 6 | 5 | 7 | 6 | | 9/11/2006 | |
| | Individual 2 | | 133 | 6/20/2006 | 0 | | 0 | | 0 | | 0 | 0 | | | |
| | Individual 3 | | 133 | 6/20/2006 | | | 3 | | 3 | | | | | | |
| | Individual 4 | | 133 | 7/28/2007 | 7 | 4 | 7 | 4 | 7 | 4 | 8 | 8 | 7/28/2007 | 7/31/2007 | |
| | Individual 5 | | 133 | 6/20/2006 | 0 | 0 | 0 | 0 | 0 | 0 | 0 | 0 | | | |
| | Individual 6 | | 133 | 6/20/2006 | 0 | 0 | 0 | 0 | 0 | 0 | 0 | 0 | | | |
| | Individual 7 | | 133 | 8/12/2006 | 6 | 4 | 8 | 4 | 4 | 4 | 5 | | | | |
| | Individual 8 | | 133 | 6/20/2006 | 3 | 2 | 0 | 0 | 2 | 3 | 0 | 0 | | | |
| | Individual 9 | | 133 | 6/16/2006 | | | | | | | | | | | |
| | Individual 10 | | 133 | 6/20/2006 | 5 | 3 | 0 | 1 | 3 | 5 | 6 | 5 | | | |
| | | | 133 | 9/30/2006 | 6 | 2 | 3 | 1 | 7 | 6 | 5 | 5 | | | |
| | Individual 11 | | 133 | 6/20/2006 | 0 | | 6 | 10 | 6 | 10 | 0 | | | | |
| | Individual 12 | | 133 | 6/21/2006 | 4 | | 4 | 2 | 0 | | 0 | | | | |
| | Individual 13 | | 133 | 6/20/2006 | 4 | 7 | 6 | 8 | 4 | 7 | 5 | 7 | | 6/22/2006 | |
| | Individual 14 | | 133 | 6/2/2007 | 10 | 10 | 10 | 10 | 10 | 10 | 10 | 10 | 7/28/2007 | 7/29/2007 | |
| | Individual 15 | | 133 | 6/20/2006 | 0 | | 0 | | 0 | 0 | 0 | | | | |
| | Individual 16 | | 133 | 7/28/2007 | 0 | | 5 | | 0 | 0 | 0 | | 7/28/2007 | | |
| | Individual 17 | | 133 | 6/20/2006 | 0 | 0 | 5 | 7 | 0 | 0 | 5 | 5 | | | |
| | Individual 18 | | 133 | 6/20/2006 | 6 | 6 | 5 | 5 | 7 | 8 | 8 | 8 | | 6/22/2006 | |
| | Individual 19 | | 133 | 6/20/2006 | 5 | 5 | 6 | 5 | | | | | | | |
| | Individual 20 | | 133 | 6/20/2006 | 0 | 1 | 0 | 1 | 4 | 2 | 1 | 1 | | | |
| | Individual 21 | | 133 | 6/20/2006 | 6 | 5 | | | | | | | | | |

FIG. 6

SB Auto Data Sorted by Personal

| Evaluation | Neck | Wrist | Back | Feet |
|---|---|---|---|---|
| Baseline | 4.09 | 3.59 | 3.71 | 3.26 |
| 1 Follow-Up | | | | |
| 2 Follow-Ups | | | | |
| 3 Follow-Ups | | | | |
| 4 Follow-Ups | | | | |
| 5 Follow-Ups | | | | |

Routine For: Automation
Created By: REMEDY PACIFIC

Nov 08, 2007
STARStretch™ - Patent Pending

FIG - 8

Routine For: GENERAL GUIDELINES
Created By: REMEDY PACIFIC

Apr 21, 2006
"Helping Hands" Stretching Program

---

EXERCISE INSTRUCTION
Avoid Overdoing

Please consult your health care provider prior to beginning for approval if you are under a physician's care.

If you experience pain while doing any of the exercises, consult your health care provider before resuming the program.

It is important to follow the repetitions as recommended in your exercise instructions in order to avoid overdoing. Also, build up your tolerance by increasing by no more than one repetition a day until you reach the maximum recommended.

Developing Routine

You may feel some tightness in your movements when you first begin the program. It takes persistence and patience to work toward your goal.

Do these exercises DAILY to get the best results. Develop a routine of doing them at a certain time of the day as much as possible.

---

Fitness

Keep fit and maintain flexibility through a regular exercise program such as walking. Weight control is also essential.

Proper Breathing and Posture

It is important that you breathe normally while doing your exercises, and avoid holding your breath.

Maintain good posture and proper head alignment when performing the exercises.

---

GENERAL GUIDELINES - Modifications for Beginners
(or Those with Back / Neck / Knee Concerns)

1. With limited knee mobility or tight hips, cross legs at ankle instead of folding them in.

2. Neck may be straight instead of turned or arched.

3. Hands may be on hips instead of reaching.

4. Legs may be slightly bent instead of straight.

5. Range of motion may be reduced.

6. Length of time in a position may be reduced.

7. May use wall or chair to help balance.

GENERAL GUIDELINES - Tips

1. Listen to your body and proceed at your own pace.

2. Breathe through the nose only using full, deep breaths.

3. Never force a position, grip, or pull while practicing.

4. In general, exhale into positions of torso flexion, inhale into positions of torso extension.

5. In general, wide stance is:

3.5 - 4 ft. for people 5'2"-5'8"
   4 - 4.5 ft. for people 5'8"-6'
   4.5 - 5 ft. for people 6'-6'5"

Beginners will start closer in than those more practiced.

6. Flexion of the torso over the legs should be a hinge from the hip. The pelvis and back stay in the same line.

FIG - 9 (page 1/4)

FIG - 9 (page 2/4)
STARStretch™ Program Questionnaire

We are interested in learning if your comfort at work has improved as a result of the stretching program. Please rate improvements below while taking into consideration your level of improvement from the beginning of the stretching program at your workplace.

> Please use blue or black ink and fill in circles like this ●,
> NOT like this ✗ ✓ ⊙

PLEASE RATE YOUR IMPROVEMENT FROM START OF PROGRAM

| Area of Body | Does Not Apply | No Improvement | Slight Improvement | Moderate Improvement | Great Improvement |
|---|---|---|---|---|---|
| Neck, Upper Back Shoulders | O | O | O | O | ● |
| Wrist, Hands, Arms | O | O | O | ● | O |
| Legs, Lower Back | O | O | ● | O | O |
| Feet | O | O | ● | O | O |

Has the stretching program improved how you feel at work?
O None   O Slight   O Moderate   ● Great improvement Has the stretching program made you feel more productive?
O None   O Slight   O Moderate   ● Great improvement Has addressing body mechanics/work methods improved safe employee work practices?
O None   O Slight   O Moderate   ● Great improvement ✱ Has stretching helped to decrease injuries and accidents in the work place?
O None   O Slight   ● Moderate   O Great improvement Are there other areas you feel need to be stretched?  MORE LOW BACK (I FEEL) WOULD BE HELPFUL What do you think of the stretching program?  GREAT FOR PAIN RELIEF, INJURY PREVENTION & MORALE - ALL EMPLOYEES SHOULD DO THIS FOR THEIR OWN BENEFIT How long have you been participating in the stretching program?  10 MONTHS (SINCE HIRED)

Do you support the stretching program?  YES!

Comments:  IT SHOULD PERHAPS BE EMPHASIZED TO SOME EMPLOYEES THAT STRETCHING IS FAR MORE EFFECTIVE IF THE STRETCHES ARE PERFORMED PROPERLY. (SOME MEMBERS OF MANAGEMENT COULD TAKE STRETCHING MORE SERIOUSLY.)

May we use your comments with your name?  ● Yes   O No, please keep my comments anonymous

CONFIDENTIAL

| REMEDY PACIFIC LICENSED OCCUPATIONAL PROFESSIONAL ERGONOMIC HEALTH SERVICES | Work Methods Training | | | |
|---|---|---|---|---|
| | Employee Name: | | Therapist: | |
| | Job Title: Collections R. | | Date: 2/28/07 | |

Location of Soreness/Fatigue: ☐ Hand ☐ Elbow/Forearm ☐ Shoulder ☒ Neck
☐ Knee ☐ Ankle/Foot ☐ Upper Back ☐ Low Back

Reported Job Function Difficulties:
1. None Reported
2. _____
3. _____
4. _____

CONCERNS:
1. Upper trapezius & supra/infra spinatus pain deep in scapula region (bilateral)
2. Holding tension in neck/shoulder region during activities
3. _____
4. _____

INTERVENTIONS:

| | Work Methods Instruction/Training | X | Body Mechanics Instruction/Training |
|---|---|---|---|
| X | Work Stretches (handouts provided) | X | Home Stretches (handouts provided) |
| | Work-Related Strengthening (handouts provided) | X | Posture Education/Training |
| | Job Rotation/Modification (as discussed w/mgmt): | | |

TBC

Equipment Recommendations:(Approved by management)

| Equipment | Source(s)* | Cost* |
|---|---|---|
| | | |

General Recommendations:
1. Use hot/heat packs pre work (use microwave at work)
2. 
3. Incorporate tension awareness + breathing
4. into daily activities
5. Deep tissue massage preferably x1/wk to
6. back, scapula + shoulder region
7. HEP as given The above has been reviewed and discussed with the employee. All are in agreement with the Findings, Interventions, and Recommendations.

SIGNATURES:
Therapist: _____ Date 2/28/07

Employee: _____ Date _____

FIG - 9 (page 3/4)

| EVALUATION | Yes/No | % of frequency of task |
|---|---|---|
| Are actions performed with sudden or jerking movement? | N/A | |
| Are tasks performed in an unbalanced and/or uncomfortable position? | | |
| Is there repetitive bending, twisting, or overreaching? | | |
| Is a load shared unevenly between both hands, or lifted by one hand only? | | |
| Does the task require a full range of joint movement which is prolonged or repetitive? | | |
| Is there a need to bend over to one side to lift or move an object? | | |
| Is an object pushed or pulled across the front of the body? | | |
| *Posture, working height, working technique, duration, frequency and other work actions and movements are all affected by the positioning of the workstation(s), equipment, controls, displays, tools and other material in relation to each other and in relation to the employee.* | | |
| Is the employee facing the task? | N/A | |
| Is the task within eye level? | | |
| Is the majority of the task within easy reach? | | |
| Does the layout fit the employee? | | |
| Does the work height fit the employee? | | |
| Is there adequate foot space? | | |
| Is the employee bending knees, keeping ears over shoulders when reaching below the waist? | | |
| Is there repetitive reaching above the shoulder? | | |
| Is the employee pivoting on feet? | | |
| *Watch for reaching above shoulder level, forward bending, extending elbow 180 degrees, twisting, and bending sideways from the waist.* | | |
| If the employee wears gloves, do they fit snugly to the hands? | | |
| Are employees practicing safe work methods? | | |
| If not why?_____ | | |
| Are there a sufficient number of employees to meet the deadline? (Ask        ) | | |
| Is there a good team effort? | | |

FIG - 9 (page 4/4)

FIG. 10 (Page 1/2)

| Opt Out | Last Name | First Name | P/L | Date | PAIN (Neck) | FREQ (Neck) | PAIN (Wrist) | FREQ (Wrist) | PAIN (Back) | FREQ (Back) | PAIN (Feet) | FREQ (Feet) | WHT Date | EI Date | Therapist |
|---|---|---|---|---|---|---|---|---|---|---|---|---|---|---|---|
| | Individual 1 | | 133 | 8/12/2006 | 3 | 3 | 7 | 6 | 6 | 5 | 7 | 6 | | 9/11/2006 | |
| | | | 133 | 1/20/2007 | 0 | 2 | 7 | 5 | 4 | 3 | 7 | 6 | | | |
| | | | 133 | 6/2/2007 | 5 | 5 | 5 | 5 | 2 | 2 | 4 | 4 | | | |
| | | | 133 | 9/22/2007 | 3 | 3 | 6 | 6 | 3 | 6 | 6 | 6 | | | |
| | Individual 2 | | 133 | 6/20/2006 | 0 | | 0 | | 0 | | 0 | | | | |
| | Individual 3 | | 133 | 6/20/2006 | | 3 | 3 | | 3 | | | | | | |
| | Individual 4 | | 133 | 7/28/2007 | 7 | 4 | 7 | 4 | 7 | 4 | 8 | 8 | 7/28/2007 | 7/31/2007 | |
| | Individual 5 | | 133 | 6/20/2006 | 0 | 0 | 0 | 0 | 0 | 0 | 0 | 0 | | | |
| | | | 133 | 9/30/2006 | 0 | 0 | 0 | 0 | 0 | 0 | 0 | 0 | | | |
| | | | 133 | | | | | | | | | | 6/20/2007 | | |
| | | | 133 | | | | | | | | | | 7/27/2007 | | |
| | Individual 6 | | 133 | 6/20/2006 | 0 | 0 | 0 | 0 | 0 | 0 | 0 | 0 | | | |
| | Individual 7 | | 133 | 8/12/2006 | 6 | 4 | 8 | 4 | 4 | 4 | 5 | 5 | | | |
| | Individual 8 | | 133 | 6/20/2006 | 3 | 2 | 0 | 0 | 2 | 3 | 0 | 0 | | | |
| | Individual 9 | | 133 | 6/16/2006 | | | | | | | | | | | |
| | Individual 10 | | 133 | 6/20/2006 | 5 | 3 | 0 | 1 | 3 | 5 | 6 | 5 | | | |
| | | | 133 | 9/30/2006 | 6 | 2 | 3 | 1 | 7 | 6 | 5 | 5 | | | |
| | Individual 11 | | 133 | 6/20/2006 | | 5 | 6 | 10 | 6 | 10 | | 9 | | 8/28/2006 | |
| | | | 133 | 8/12/2006 | 4 | | 8 | 9 | 7 | 5 | 6 | | 3/13/2007 | | |
| | | | 133 | | | | | | | | | | | | |
| | | | 133 | 6/2/2007 | 6 | 5 | 8 | 6 | 3 | 3 | | | | | |
| | Individual 12 | | 133 | 6/21/2006 | 0 | | 4 | 2 | 0 | | 0 | | | | |

FIG. 10 (Page 2/2)

| Opt Out | Last Name | First Name | P/L | Date | PAIN (Neck) | FREQ (Neck) | PAIN (Wrist) | FREQ (Wrist) | PAIN (Back) | FREQ (Back) | PAIN (Feet) | FREQ (Feet) | WHT Date | EI Date | Therapist |
|---|---|---|---|---|---|---|---|---|---|---|---|---|---|---|---|
| | Individual 13 | | 133 | 6/20/2006 | 4 | 7 | 6 | 8 | 4 | 7 | 5 | 7 | | 6/22/2006 | |
| | | | 133 | 8/12/2006 | 3 | 3 | 3 | 2 | 4 | 4 | 5 | 4 | | | |
| | | | 133 | 9/30/2006 | 5 | 2 | 7 | 2 | 5 | 2 | 5 | 2 | | | |
| | | | 133 | 11/18/2006 | 5 | | 5 | | 3 | | 5 | | | 11/22/2006 | |
| | | | 133 | 1/20/2007 | 1 | 1 | 1 | 1 | 3 | 1 | 3 | 1 | | | |
| | | | 133 | 6/2/2007 | 2 | | 3 | | 3 | | 3 | | | | |
| | | | 133 | 9/24/2004 | 4 | | 4 | | 4 | | 5 | | | | |
| | Individual 14 | | 133 | 6/2/2007 | 10 | 10 | 10 | 10 | 10 | 10 | 10 | 10 | 7/28/2007 | 7/29/2007 | |
| | | | 133 | | 10 | 10 | 10 | 10 | 10 | 10 | 10 | 10 | 8/31/2007 | | |
| | Individual 15 | | 133 | 6/20/2006 | 0 | | 0 | | 0 | | 0 | | | | |
| | | | 133 | 6/15/2007 | 0 | | 0 | | 4 | 4 | 0 | | 6/15/2007 | 6/20/2007 | |
| | Individual 16 | | 133 | 7/28/2007 | 0 | | 0 | | 0 | | 0 | | 7/28/2007 | | |
| | Individual 17 | | 133 | 6/20/2006 | 0 | 0 | 5 | 7 | 0 | 0 | 5 | 5 | | 8/22/2006 | |
| | Individual 18 | | 133 | 6/20/2006 | 6 | 6 | 5 | 5 | 7 | 8 | 8 | 8 | | 6/22/2006 | |
| | Individual 19 | | 133 | 6/20/2006 | 5 | 5 | 6 | 5 | | | | | | | |
| | Individual 20 | | 133 | 6/20/2006 | 0 | 1 | 0 | 1 | 4 | 2 | 1 | 1 | | | |
| | Individual 21 | | 133 | 6/20/2006 | 6 | 5 | | | | | | | | 9/11/2006 | |
| | | | 133 | | | | | | | | | | | | |
| | Individual 22 | | 133 | 6/20/2006 | 7 | 7 | 8 | 7 | 7 | 7 | 7 | 7 | | 6/22/2006 | |
| | | | 133 | 9/30/2006 | 9 | 9 | 9 | 8 | 9 | 9 | 9 | 9 | | | |
| | | | 133 | 6/2/2007 | 10 | 10 | 10 | 10 | 10 | 10 | 10 | 10 | | 10/28/2006 | |

FIG. 11

| SB Auto Data Sorted by Personal Flw-up # | | | | |
|---|---|---|---|---|
| Evaluation | Neck | Wrist | Back | Feet |
| Baseline | 4.09 | 3.59 | 3.71 | 3.26 |
| 1 Follow-Up | 4.09 | 3.91 | 3.61 | 3.27 |
| 2 Follow-Ups | 3.90 | 3.60 | 3.76 | 3.20 |
| 3 Follow-Ups | 2.86 | 3.51 | 2.86 | 2.37 |
| 4 Follow-Ups | 3.17 | 3.24 | 3.12 | 3.19 |
| 5 Follow-Ups | 3.00 | 3.52 | 2.95 | 2.67 |

OCCUPATIONAL THERAPY AND ERGONOMIC SYSTEM

CROSS-REFERENCE TO RELATED APPLICATIONS

This is a standard utility application that claims priority from U.S. Provisional Application Ser. No. 60/868,040, filed Nov. 30, 2006, the entire disclosure of which is incorporated herein by reference.

BACKGROUND OF THE INVENTION

1. Technical Field

This invention generally relates to the field of occupational health and safety. More particularly, the invention relates to a health modality for corporations. Specifically, the invention relates to a program incorporating a combined occupational therapy and ergonomic modality in a company that is designed to proactively reduce the number of injuries to employees which could be caused by their normal work-related activities.

2. Background Information

Employees in a variety of industries may be required to perform repetitive motions, employ force to push or pull heavy objects, assume or hold awkward positions or may have to push parts of their body against hard or sharp objects in the performance of certain tasks on the job. Some of these procedures may result in the employee becoming injured over a period of time. In many instances, the equipment the employee is using is not designed in an ergonomic manner and, consequently, habitual use of that equipment leads to injury. So, for example, if a factory employee has to habitually and frequently reach for a piece of equipment, they will tend to develop muscle fatigue and possible injury of the reaching arm. If such an injury occurs, the employee will be less productive and will possibly have to be relieved of that position for a period of time. The employee may also have to be sent to doctors, physiotherapists or occupational therapists for rehabilitation before they can return to work.

There is a substantial amount of effort devoted to assisting industry to make the workplace a safe and healthy environment for employees. Most of this effort is directed to addressing practices and procedures that cause musculoskeletal disorders in particular. This focus, known broadly as ergonomics, studies how people perform their daily tasks and how to minimize the stresses and strains caused by repetitive motion, bending, lifting, maneuvering the body and the effect of machines and other tools that tend to increase the likelihood of musculoskeletal problems developing. Ergonomists are trained to assess how a particular type of employee conducts their daily tasks and will make suggestions as to how better to perform a task or alter equipment in order to reduce the possibility of injury. A wealth of information and professionals are available to assist industries to address ergonomic issues. For instance, OSHA, which is the Occupational Safety and Health Administration of the United States Department of Labor, has published industry and task specific guidelines for grocery retailers. These guidelines have been produced in response to the evaluation of many years of data from the grocery industry and include suggestions as to how to perform standard grocery store tasks such as lifting objects during shelf stocking or working at a cash register, in a less injurious fashion.

Even with this wealth of information and such guidelines in place, some equipment cannot be modified to be ergonomic and some tasks can only be modified to a certain degree to make them more user-friendly. Consequently, numerous employees become injured on the job every year and have to face and overcome those injuries. There is, once again, a wealth of information and professionals available to aid people in recovering from musculoskeletal-type injuries after they have occurred. These professionals include doctors, physiotherapists, occupational therapists and chiropractors, just to name a few. The injured employee may suffer a lot of pain, lose income and may also have to relearn how to do their job in a different way in order to recover. Additionally, the employer will likely have had a drop in productive activity from that injured employee and possibly had to pay for rehabilitation and recovery time for that employee. All of this drives up the cost of doing business and results in much pain and economic distress for the employee.

There is therefore a need in the art for an improved system of addressing the potential for musculoskeletal and other injuries to employees that might be caused by job-related activities.

SUMMARY OF THE INVENTION

The present invention comprises a proactive and progressive therapeutic system which combines the preventative and healing measures of ergonomics with the healing measures of occupational therapy. The program is designed to be implemented in a business in order prevent the employees from becoming injured on the job, instead of waiting until the employees are injured and then addressing the issue.

The system of the present invention comprises identifying a company which will benefit from the system and approaching the same with a business proposal. Once hired, an occupational therapist evaluates the company's workplace environment and an initial physical state of a group of employees employed by the company; assesses data gathered during the evaluation; develops a corrective therapeutic program to address areas of concern identified during the assessment; implements the corrective therapeutic through instruction of the employees; and conducts periodic follow-up evaluations, adjusting the corrective therapeutic program as required until the outcomes of the system are achieved.

The system designed to be marketed to businesses is useful for detecting and evaluating potentially injurious activities, setting up an ergonomic program to reduce the number and type of those activities, and setting up a preventative-rehabilitation program for employees who perform these potentially injurious activities. The program also includes setting up an initial series of stretches for employees with a risk for a particular injury, teaching that initial series of stretches to all employees who perform the potentially injurious tasks, evaluating the employees after a period of time, assessing the results of the evaluation and adjusting the stretching program by increasing the intensity and/or types of stretches. The cycle of evaluation, assessment and stretch therapy adjustments will be continued until the employees have the fullest range of motion possible and are as injury free as possible. The program is designed for evaluating each individual that performs a particular job, assessing those results, combining the results of all of the individuals who perform the tasks and assessing the most common injuries and body areas that the individuals in the group are experiencing and developing a program of stretching to address those most common problem areas of the body. If a particular individual is found to be further down the slope toward becoming injured or less able to cope with the developed program, the therapist will customize the stretching program to pay special attention to the individual's problem areas.

A primary object and feature of the present invention is to provide systems and methods for creating an occupational therapy and ergonomics program for preventing injury to persons performing a variety of tasks.

A further object and feature of the present invention is the identification of potential businesses that employ a plurality of employees who perform potentially injurious tasks and offering those identified businesses the opportunity to implement the combined occupational therapy and ergonomics program.

A further object and feature of the present invention is the identification and evaluation of particular jobs in that business that have the potential for employees to become injured while performing the tasks of that job. The systems and methods include having the persons perform the tasks and noting discomfort in various bodily areas that arise from performance of the same. The evaluation is provided through a variety of means that includes but is not limited to observation of the employees performing the tasks, physically testing the employees, conducting personal interviews with employees; and providing employees with a variety of printed questionnaires to be completed by them.

A still further object and feature of the present invention is assessing the data gathered during the evaluation procedure. The assessment includes but is not limited to reviewing the information gathered through observation, physical tests, interviews and questionnaires, and analyzing the data obtained therefrom.

A still further object and feature of the present invention is the development of a progressive program specifically designed to address the issues that emerge from the assessment. The development includes but is not limited to providing instruction as to how to ergonomically alter the tasks and selecting a range of stretches of ever increasing difficulty and intensity to alleviate discomfort and pain experienced by the employees and to reduce the possibility for further injury.

Another object and feature of the present invention is to provide instruction as to the type of stretches that will reduce the tendency for the employee to become injured. The instruction is provided through a variety of means that includes but is not limited to demonstration, and providing printed instructional sheets and diagrams explaining how to perform the selected stretches.

A still further object and feature of the present invention is to conduct follow-up evaluations of the employees through a range of means including but not limited to conducting personal interviews, conducting tests and providing employees with a variety of printed questionnaires to be completed.

Other objects and features of this invention will become apparent with reference to the following description.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

FIG. 3 is a sample baseline form, the first page is completed by the employee to give a baseline pain level, the second to seventh pages are completed by the therapist during the initial ergonomic and occupational therapy evaluations of the group of employees performing one particular job;

FIG. 4 is a sample of a completed baseline form that has been completed by the employee and therapist during the ergonomic and occupational therapy evaluations of a job and includes an explanation of the therapists observations (seven sheets in all);

FIG. 5 is a sample of a printout of compiled data gathered during the evaluation process with the names of the employees involved changed to Individual's 1-21 to protect the privacy of the evaluated employees;

FIG. 6 is a printout of a baseline average pain level experienced by group of employees as gathered from a Discomfort Baseline Questionnaire which forms part of the initial evaluation forms;

FIG. 7a is a sample of a Level 2 sheet of stretches produced for employees working the Automation job, and showing illustrations of stretches that are more challenging than those illustrated in FIG. 7;

FIG. 7b is a sample of a Level 3 sheet of stretches produced for employees working the Automation job, and showing illustrations of stretches that are more challenging than those illustrated in FIG. 7a;

FIG. 7c is a sample of a Level 5 sheet of stretches produced for employees working the Automation job, and showing illustrations of stretches that are more challenging than those illustrated in FIG. 7b;

FIG. 8 is a general guideline sheet (FIG. 8) that will be provided to each individual employee who does job 26a as part of the reminder package given to them during the teaching stage of the system;

FIG. 9 is a sample of four sheets used as part of a follow-up evaluation, with pages 1 and 2 of this figure being forms that are filled out by the employees, and pages 3 and 4 being forms that the therapist may use in their follow-up evaluation of the group of employees;

FIG. 10 is a sample of a printout of compiled data gathered during both of the baseline and follow-up evaluation process with the names of the employees involved changed to Individual's 1-22 to protect the privacy of the evaluated employees (two sheets); and FIG. 11 is a printout summary of a baseline average pain level experienced by group of employees as gathered from the initial baseline evaluation through several follow-up evaluations and most specifically from the baseline and follow-up Discomfort Questionnaires completed by the employees.

DETAILED DESCRIPTION OF THE INVENTION

Figure 1:
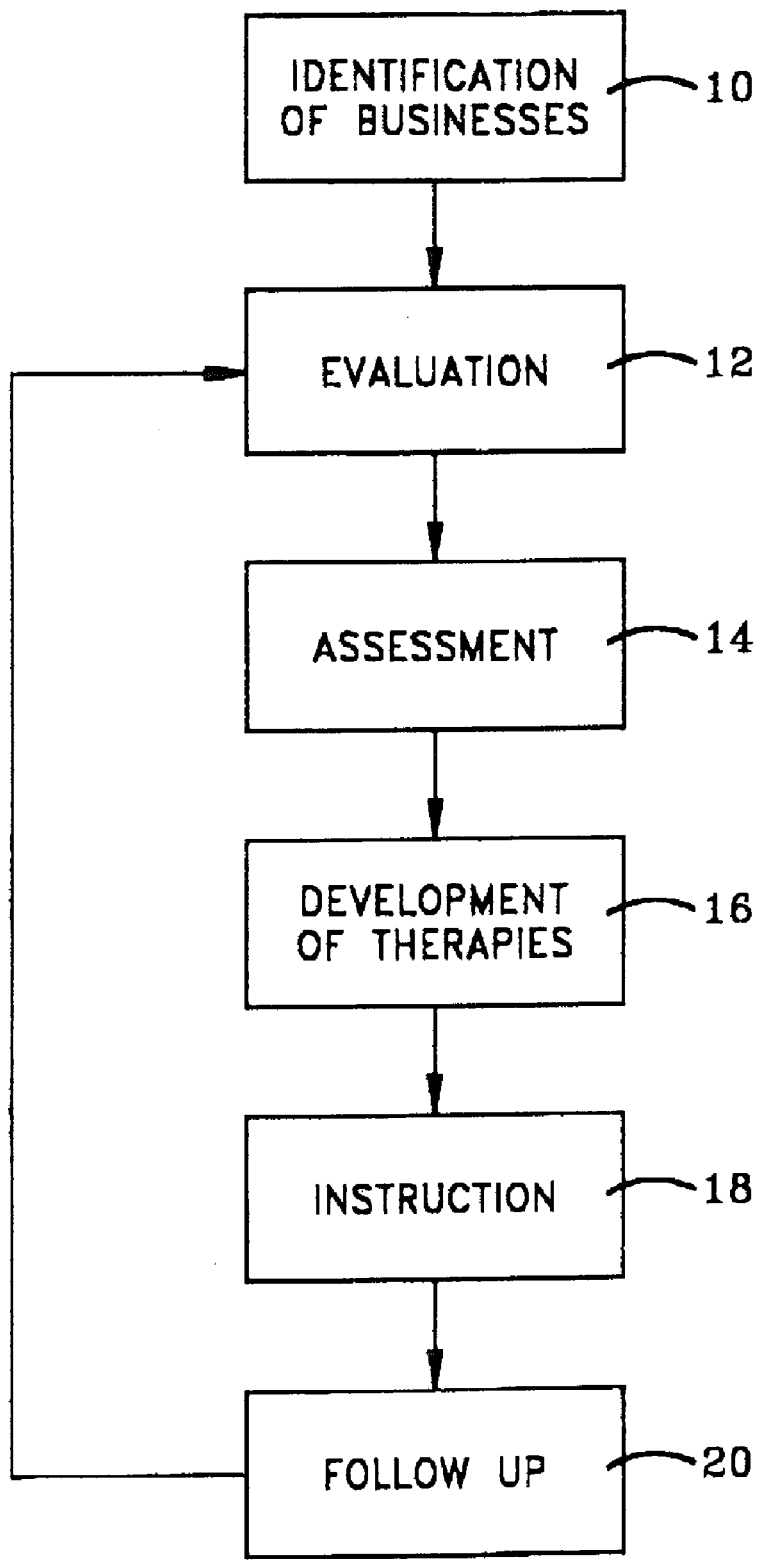
FIG. 1 is a high-level logic diagram for a technique for creating an occupational and ergonomic therapy program for implementation in a business in order to heal and prevent injury in persons performing a variety of jobs.

Referring to FIG. 1, the present invention is a system for creating and implementing a combined occupational therapy and ergonomic modality for a workplace so as to proactively prevent injuries to employees of a company during their normal work-related activities. The system involves the implementation of six steps which are briefly summarized hereinafter and are then discussed in greater detail. These steps are:

Step 1, which is generally indicated in FIG. 1 by the number 10, involves the identification of a company that would benefit from the system and approaching that company to offer them a business proposal, namely offering them the service of developing and implementing a preventative modality to aid in preventing injury to their employees while they are conducting their normal work-related activities.

Presuming that the approached business is interested, Step 2 involves the evaluation of the workplace environment and the initial physical state of the employees employed by the business. This step is referenced by the number 12 in FIG. 1.

Step 3 involves the assessment of the data gathered during Step 2 and is referenced by the number 14.

Step 4 involves developing a corrective therapeutic program to address areas of concern identified during the assessment step, and is referenced by the number 16 in FIG. 1.

Step 5, referenced by the number 18 in FIG. 1, involves implementing the corrective therapeutic through instruction of the employees.

Finally, Step 6 involves conducting periodic follow-up evaluations and adjusting the corrective therapeutic program as required. Step 6 is referenced by the number 20 in FIG. 1 and requires the repetition of Steps 2 through 5 until the desired outcomes of the program are achieved and a desired threshold of improvement from the initial physical state of the group of employees is reached. The outcomes of the program are the minimization of injurious activities identified during the evaluation to reduce the possibility of the employees becoming injured during their normal work-related activities; relief of task-generated pain identified during the evaluation, and the healing of physical deterioration in employees who may not yet be classified as injured.

Each step in the system will now be described in greater detail hereinafter.

Step 1 is the identification of potential customers. This is done by selecting companies who employ people who are potentially at risk of musculoskeletal injury on the job because of repetitive type tasks, tasks involving strength, lifting, twisting or contact with hard or sharp objects, amongst others. An example of a possible suitable customer would be any manufacturing facility that utilizes manned assembly lines in the production of a product. The assembly line may include, for example, employees that monitor articles moving along conveyors and who have to repetitively reach across the conveyor to remove defective articles. Another possible suitable customer is any business where employees operate some type of machinery or equipment and that machinery requires them to repeat the same steps over and over. A third example of a possible customer is any business, such as a postal sorting station, where the employees may be lifting heavy objects, such as parcels, moving heavy loads from one location to another, or working at a service desk where the same motions are repeated every time a customer is served. Generally speaking, any manufacturing or processing facility would be a suitable candidate for implementation of the present invention. As will be understood, many service-related industries and industries who employ office workers will also be suitable candidates for this therapeutic program. Office jobs, such as typing on a computer, are notorious for causing injuries such as carpal tunnel syndrome.

The therapist may utilize a wide variety of readily available resources to locate such suitable business candidates. These resources include, but are not limited to performing online searches via the Internet, visiting the library or local Better Business Bureau and conducting searches for manufacturing or processing facilities in any particular region, or through networking through acquaintances who may have business contacts. Online searches via the Internet may be conducted by utilizing search engines such as Google® owned and operated by Google Inc. of Mountain View, Calif. and located at www.google.com on the Internet; Yahoo® owned and operated by Yahoo! Inc. Of Sunnydale, Calif. and located at www-.yahoo.com; or specialized manufacturer directors such as that available at www.thomasnet.com which is owned and operated by Thomas Publishing Company of New York, N.Y. These search engines can be searched by entering appropriate keywords to aid in finding a suitable business candidate. For example, if the therapist wanted to find manufacturers of bolts, they would enter the keywords bolts and manufacturers on the search line of the search engine, hit enter and then review the results found by the search engine. A search may also be conducted by reviewing any number of directories of manufacturers located in the Reference Section of any local library. A desired type of manufacturer can be located in the index of the directory and specific companies can be found by turning to the pages identified in the index of the directory and reviewing the lists of companies compiled therein.

After a group of suitable business candidates has been identified, those companies are approached via letter, telephone calls, meetings and other known methodologies for offering a service to a business.

Figure 2:
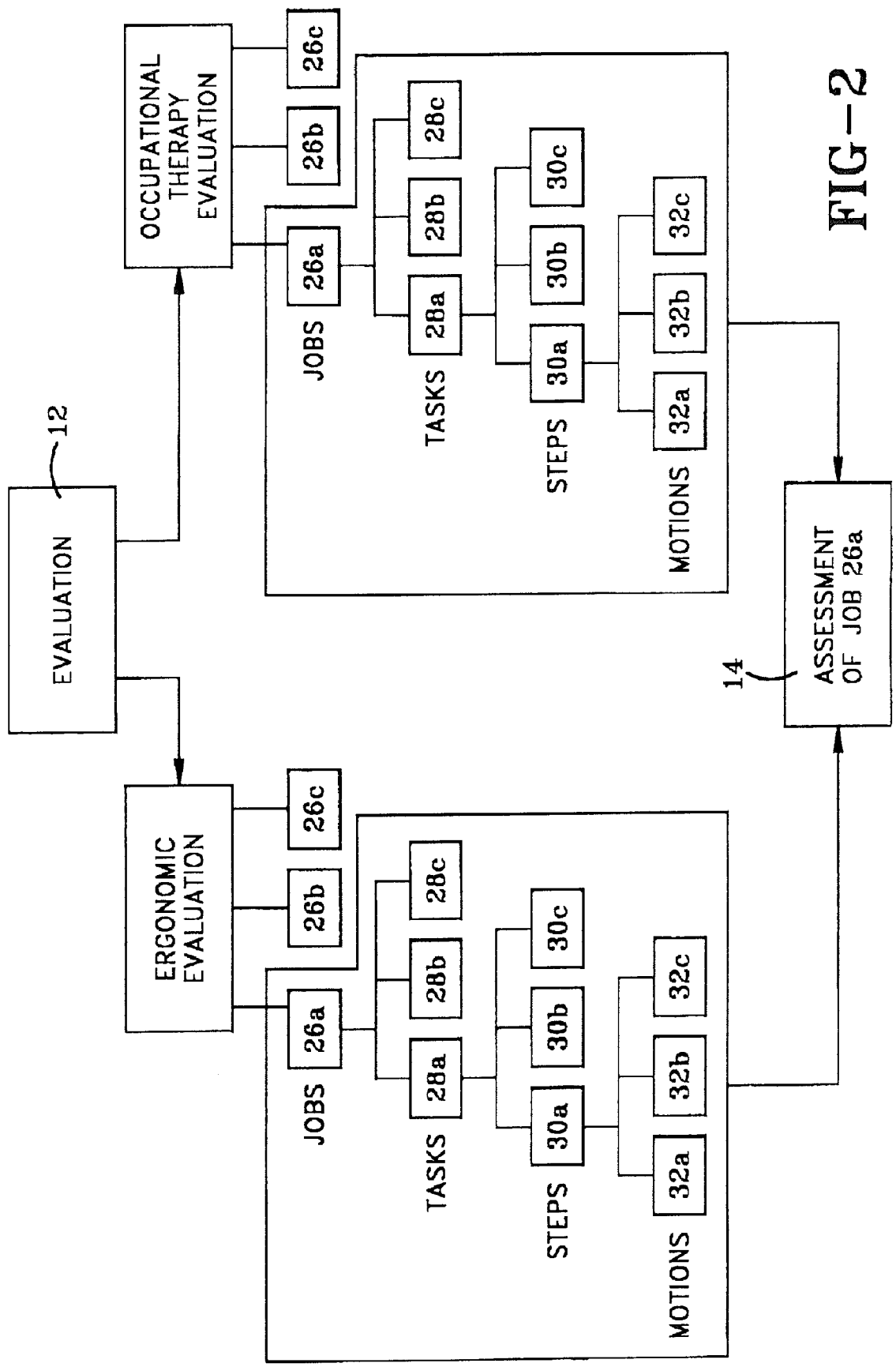
FIG. 2 is a diagram illustrating the two-pronged evaluation procedure for gathering information about a specific job.

Once the step of identifying a suitable company 10 has been accomplished and that company has agreed to hire the therapist, then Step 2 of the present system is undertaken. Step 2 involves an evaluation 12 of the identified business 10. As shown in FIG. 2, Step 2 is a two-pronged evaluation procedure that involves the gathering of information from the identified business and its employees on a number of different fronts. Essentially, the health modality involves identifying jobs and job tasks that put employees at risk for injuries caused by repetitive motion, bending, lifting, and maneuvering of the body alone and in relation to any machinery and equipment used to perform those job tasks. The evaluation 12 includes the prongs of an ergonomic evaluation 22 and of an occupational therapy evaluation 24.

In accordance with a specific feature of the present invention, the instant inventor has developed a set of forms and questionnaires that are supplied and used by the therapist during the ergonomic and the occupational therapy evaluations 22, 24. These forms are completed when the therapist conducts the evaluations 22, 24. It should be noted that not all forms will be relevant to each job situation being evaluated and the therapist will select the appropriate forms for use in any particular situation. A sample set of forms is shown in FIG. 3. FIG. 3, page 1 is a form that is completed by the employee, with the therapist involved only to the point of ensuring that the employee is accurately identified thereon. FIG. 3, pages 2 through 7 are completed by the therapist during the initial evaluation of a group of employees and the job tasks they are assigned to do. Not all seven pages of the forms shown in FIG. 3 have to be completed for each individual employee that is observed and evaluated, although this could be done.

The ergonomic evaluation 22 involves the therapist identifying a plurality of jobs in the workplace, such as jobs 26*a*, 26*b* and 26*c*. Each job 26*a*, for example, is closely observed to identify the various tasks 28*a*, 28*b*, 28*c* that have to be undertaken to perform that job. Each task, 28*a* for example, is then broken down into the specific steps 30*a*, 30*b*, 30*c* that need to be taken to do the task 28*a*. Then, each of the steps 30*a*-30*c* is broken down into the motions 32*a*-32*c* required to perform those steps. Additionally, the therapist must consider a range of other risk factors that might affect the employees performing the tasks, jobs, steps and motions. These can include the methodology that must be followed to perform the task, the effort or strength required, the location of parts, equipment and tools and the relative positions of the same, the speed and frequency of the work, the duration and repetition of the tasks and the design of the tools and machinery to be used on the job. Additional factors such as lighting, noise, temperature and air quality are also of importance and should be notes. The therapist needs to also consider and note any awkward body positions and heights that might have to be adopted or sustained on the job. The employee might also have to continuously reach above shoulder height, bend over, twist or make movements which take certain muscle groups to the employee's outer limits of their range of motion. For most people, precision type tasks are best performed at or slightly above elbow height and with the elbows adequately supported. Work requiring force to be applied is best down when the workpiece is situated below elbow level. The work should ideally also be in a comfortable visual range. These are some of the many factors that are of importance and need to be noted by the therapist.

All of the ergonomic type of information is gathered by a combination of observation and interview of as many individuals in the group of employees who do a particular job as is possible.

The therapist also conducts the occupational therapy evaluation 24, likely alongside the ergonomic evaluation 22 and completes the provided forms and questionnaires as they conduct this evaluation 24. For each job, such as job 26a, the therapist evaluates the body movements required to perform job 26a, tasks 28a-c, steps 30a-30c and motions 32a-32c and notes any areas of concern relating to the employee's muscles, joints and other body parts to determine which body areas might potentially be injured while performing job 26a. The therapist also conducts a variety of known occupational therapy tests to determine the ranges of motion that each individual employee is able to accomplish for each appropriate body part used in the performance of the job 26a. All of this information is recorded on the provided forms (FIG. 3).

In the sample set of forms used in the Evaluation 12 and shown in FIG. 3, page 1 is a Discomfort Questionnaire that is completed by each individual employee. Preferably, the therapist will fill out the employee identification section of the questionnaire by completing the pay location, work ZIP code and employee ID numbers, such as the employee's social security number, by darkening the appropriate circles on the form. The date of the interview and observation is also recorded in a similar manner. The employee will complete the remaining portion of the form indicating their pain level and pain frequency numbers by darkening the appropriate circles on the form. These pain numbers relate to issues the employee is having in regard to their neck, shoulders, upper back, wrists, hands, arms, lower back, legs, feet and other areas of their body. The name of the individual is filled in on the form and the comments section is completed.

The combined observation, interview and testing phase of the evaluation is then conducted. The therapist will have one or more of the employees demonstrate their daily tasks over and over and the therapist will record their observations on the appropriate pages of the form. So, for example page 3 of this form constitutes part of the ergonomic evaluation 12 and the therapist will complete each line on the form that applies. For instance, in response to the question on page 3, "Is the employee facing the task?", the therapist will complete the form by filling out, in the first column provided, a "Yes" or a "No" answer. In the next column on the form, the therapist will record their estimate of the percentage frequency of the task by filling in the appropriate percentage, for example "50%". Similarly, on page 4 of the form, which constitutes part of the occupational therapy evaluation, under the section "Elbow and Forearm" the therapist will conduct a physical test on one or more employee to determine the flexion of the tested employee's arm and will fill in the appropriate goiniometer measurements in the column provided, recording both the typical measurement and the measured end point. On page 4, for example, under the elbow and forearm flexion question at the bottom of the page, the therapist will enter, for example, "90" as the flexion measured in this particular employee.

The appropriate portions of the remainder of the form is completed in like manner. On the final page of the form, the therapist will write down their recommended interventions and equipment recommendations to this point. So, for example, if the therapist believes that the employees require "Work Methods Instruction/Training", the therapist will check off the box next to that particular recommendation. If the therapist believes some equipment needs to be changed, the type of equipment is written down in the appropriate column and the source and cost of such equipment will be filled in either at the job site or at a later date.

Once the form is completed, the therapist will sign and date the same in the place indicated. The provided forms will usually be written on directly by the therapist when observing and testing the employees at the site, but a clean typed sample copy is provided herein as FIG. 4, for the sake of clarity. Obviously, the names of the individual employees and therapist have been blacked out on the sample forms for privacy reasons, as has a portion of the employee's social security number and other information that might inadvertently lead to the identification of the person evaluated.

A review of the completed form (FIG. 4) shows the nature and type of information typically recorded during evaluation 12. If page 7 of the completed form is reviewed, for example, the boxes for "Work Methods Instruction/Training", "Work Stretches", "Work-Related Strengthening", "Job Rotation/Modification", "Body Mechanics Instruction/Training" and "Train-the-Trainer Program" have been checked off to indicate that these areas have been identified by the therapist as areas of concern for this employee. This page also shows that the therapist identified the need for an anti-fatigue mat to be supplied to this employee and indicated that the source of these mats is a "Catalog" with the price thereof "To Be Determined".

The therapist will evaluate as many individual employees who perform that particular job 26a as necessary. The information gathered on all of the forms for all of the individual employees is preferably entered into a database for analysis during the assessment phase of the process. A sample of a printout of the gathered information is shown attached hereto as FIG. 5.

The next step in the process is Step 3, the assessment 14. During the assessment step 14 an analysis is made of the combined results of all tasks 28, steps 30 and motions 32 of job 26a as recorded in the baseline questionnaires and worksheets for the total number of employees performing a particular job. The combined results can be produced by the therapist or by computer. The therapist notes any similarities in the pain and/or injuries experienced by this group of employees. This assessment may be made manually by the therapist reviewing all of the responses, or may be made by way of a computer program. A variety of known statistical tests can be run on this accumulated data to assess the results and a final evaluation result sheet summarizing the results of these tests can be printed. So, for example, if ten employees were observed and interviewed for job 26a, then on the Baseline Questionnaire, Discomfort Information, the foot pain level indicators for the ten employees are combined and the median pain level is worked out. That median pain level becomes the baseline foot pain level around which the therapist will base the stretching program. All other information on the form is combined in a similar fashion so that there is a baseline reading for each and every question answered or test conducted and a baseline assessment sheet is produced which reflects the results. An example of a sample of a sheet showing the baseline average pain level experienced by group of employees as gathered from the Discomfort Baseline Questionnaire is attached hereto as FIG. 6. This sheet is used by the therapist to identify the problem areas of potential or actual injury to employees who perform that job and the likelihood of injuries to various body parts for employees who assume that position in the future.

In the next step, i.e., Step 4, the areas of concern identified in Step 3 are matched with possible therapies. These therapies may be ergonomic in nature, such as altering a machine, or altering the motions involved in a step, or the steps involved in a task, or the tasks involved in a job. The therapies preferably also include occupational therapies and involve a plurality of stretches in order to address muscular or joint issues that have been identified in the assessment. There are many therapies known in both the field of ergonomics and the field of occupational therapy that have been proven to address certain types of problems and injuries and many of these known therapies have been compiled into databases that are available online, in books or in some other printed format from professional associations. In the past, these therapies have only been used to aid in the healing of injuries that people have already been diagnosed with. In the present invention, on the other hand, these previously known therapies are applied in a new way. This new way is utilizing this vast store of knowledge to respond to trends and patterns identified during the evaluation and assessment phases of this preventative system and apply them to people to prevent injury from normal work-related activities and preferably before there has been sufficient harm caused to the individual for an injury diagnosis to be made.

The known ergonomic therapies are designed to address work habits, tasks and equipment usages. The known occupational therapies are designed to address musculoskeletal injuries to various body parts. The present modality is therefore primarily preventative in nature as opposed to curative.

Step 4, the development of therapies 16 (FIG. 1), may be done manually by the therapist drawing on their own personal knowledge, gathering information from books or via the Internet. For example, the therapist can utilize already compiled stretching charts that are purchasable from companies such as Stretching Charts, Inc., of Tacoma Wash., who also conduct business as Visual Health Information (VHI). This company provides compiled collections of illustrations of exercises and stretches on compact disc. The collections may be purchased by medical professionals from a variety of disciplines. If the therapist elects to use such a compilation, they will review the results obtained in the assessment phase of this process and will select a range of appropriate stretches for the areas and issues of concern that have been identified. The therapist will then electronically copy the selected stretches from the compact disc, Internet source, book or professional publication, and will compile a series of sheets of illustrations to address one or more issues that have been identified for the individuals who perform job 26a, for example. The therapist will then rate each stretch and will group the stretches into subsets of different levels of difficulty. The therapist will also decide, based on their knowledge, what order the stretches in each sublet should be done in. The illustrations of the stretches will then be organized accordingly into ordered groups of stretches of progressive levels of difficulty. The illustrations for each difficulty level of stretches will be printed onto a single sheet and labeled for the order in which the stretches on the sheets of stretches should be implemented. These above steps may also be performed by computer if the therapist wishes to utilize a computer program for this purpose.

Figure 7:
FIG. 7 is a sample of a Level 1 sheet of stretches produced for employees working in an Automation job.
Figure 7B:

FIGS. 7-7c show a sample of four sheets of stretches for addressing various areas of concern identified in the evaluation and assessment phases for a particular job. The illustrations shown on these sheets are taken from a database that was purchased from VHI referenced earlier herein. FIG. 7 shows the Level 1 sheet of stretches. FIG. 7a shows the Level 2 sheet of stretches. FIG. 7b shows Level 3 and FIG. 7c shows Level 5. In this instance, the job evaluated was an automation job for a postal sorting station. The group of employees was found to have elevated pain levels in their arms, wrists and hands and so the therapist specifically located and selected an appropriate group of stretches that are designed to address such issues. The therapist determined which of those selected stretches could be done initially by the group of employees taking their baseline pain level and range of motion as a guide. This initial group of selected stretches was cut and pasted onto a single sheet of paper to form the Level 1 page shown in FIG. 7. The therapist selected a second and more difficult or challenging group of stretches that would require the employees to have a slightly improved range of motion than is the case with the Level 1 stretches. The illustrations of this second group of exercises are printed in sequence onto a second sheet of paper to form the Level 2 sheet shown in FIG. 7a. The Level 3 and Level 5 sheets (FIGS. 7b, 7c) are produced in the same manner. The therapist will continue this process until he or she has produced an entire series of sheets of progressively more difficult and challenging levels of stretches that are designed to return the employees to what would be considered by occupational therapy professionals to be a normal range of motion for a particular body area.

The therapist will then compile a teaching package to be presented to the employees of job 26a to address the issues identified in the evaluation 12 and assessment 14 phases. The progressive program may include a General Guideline Sheet (FIG. 8) that will be provided to each individual employee who does job 26a and any ergonomically related information sheets (not shown) that are deemed relevant to the job 26a by the therapist. The program will also include the Level 1 sheet (FIG. 7) of printed stretches and/or exercises that cover the initial phase of the stretching program to be followed by those employees. While not initially designed to be given to the employees, the teaching package will also include sheets that cover the progressively more difficult stretching Levels. These are held in reserve initially by the therapist. A similar type of program covering a plurality of stretching level sheets can be developed and printed for specific individuals who have been identified during the evaluation and assessment phases, as having particular issues that are not found in the rest of the group but which need to be addressed.

Step 5 of the system of the present invention involves the implementation by instruction 18 (FIG. 1) phase of the program. The individual employees who perform job 26a, for example, are gathered together. The therapist will use the teaching package sheets, specifically, the Level 1 sheets and ergonomic recommendation sheets, to teach the work habits, postures, procedures and stretches to address the identified issues. Teaching is done from a variety of approaches including discussion of the information on the sheets, observations made by the therapist during the evaluation and assessment phases, physical demonstrations of how to perform the various motions, steps, and tasks to complete the job, and the therapist will also physically demonstrate the selected stretches. The therapist will also watch each individual in the group perform the previously demonstrated job tasks and stretches and will correct and guide each individual as needed. The therapist will then select a volunteer coach from among the employees and will personally train this coach in these modalities to ensure that the employees have someone to direct and assist them when the therapist is no longer present. Furthermore, each employee will be provided with their own copy of the Level 1 stretching and information sheets that form part of the developed program. These sheets will serve as a reference for the employee, in both pictures and text, as to how to change the steps and motions they should perform while doing their job. The sheets will also remind them of which stretches they should perform to protect themselves against possible injury and show them how to do those stretches correctly.

The above procedure is performed for each at risk job 26*b*, 26*c* that has been identified in the selected company.

A predetermined period of time is allowed to pass such as a period of between two to three months. During this time period, the coach for the group of individuals who perform a particular job will then lead that group in their stretches every work day for a period of five to ten minutes. After the allotted period of time has passed, the therapist will return to the company and conduct a follow-up. This is step 6 shown in FIG. 1, and is referenced by the number 20. In the follow-up, the therapist repeats most of the original evaluation of the employees who perform job 26*a*. The only step not necessary is the step-by-step evaluation of the job 26*a* to determine what tasks, steps and motions are required to perform the job as this has been previously noted by the therapist. The therapist does have to observe the employee performing their job tasks, steps and motions, as well as interview the employees and go through the physical tests that were done for the baseline procedure. Alongside these steps, the therapist has to complete a set of follow-up forms which is essentially identical to the forms shown in FIG. 3. A sample of four sheets taken from a completed follow-up evaluation is attached hereto as FIG. 9. The first two pages, indicated as FIG. 9 (page 1/7) and (page 2/7) are completed by the employee. The pages (page 3/7) and (pages 4/7) are a sample of sheets that may be completed by the therapist if relevant. These latter two sheets might also be used by the therapist during training of the group of employees.

Once the follow-up evaluations for all the employees in job 26*a* have been completed, the steps of assessment of the evaluation results, development of therapies, instruction and follow-up are done once again. The step of development of therapies will involve the therapist reviewing the progressive stretching level sheets produced during the initial phase to ensure that it would be appropriate to implement the Level 2 stretches. The system may require that the therapist adjust the selected stretches if the assessment indicates this is necessary. In this instance, a new or reorganized group of stretches will be printed onto a sheet for the training portion of the program. The next level of stretches, or the revised program if developed, is then taught to the employees and to the coach as in the initial manner.

Once again, a predetermined period of time is allowed to pass in which the employees stretch every day and follow the next level of the program. The therapist then returns to the company and follows-up yet again. The results of the follow-ups are recorded and tracked over several months to monitor the progress of the employees of the company. FIG. 10 shows a sample of a printout of compiled data gathered during the entire evaluation process with the names of the employees involved changed to Individual's 1-21 to protect the privacy of the evaluated employees. The printout includes initial baseline data and data gathered during a series of follow-up evaluations. Attached hereto as FIG. 11 is a copy of a printout summarizing both the pain level results gathered from the initial baseline evaluation and through several follow-ups for a group of employees. As will be noted, the pain levels of all tracked body areas shows a decrease in reported pain levels by the employees of the job 26*a*.

The desired outcomes of the system of the present invention are the minimization of pain or discomfort from on-the-job activities for the vast majority of employees who do job 26*a*. Individuals who are not progressing at the same pace as the rest of the group will be given additional or alternate stretches to aid them and the therapist will continue to follow-up with these individuals or will have them referred to outside medical personnel.

This program will be implemented for each of the identified jobs 26 in the company and is designed to equip employees to self-monitor after a sustained period of training, stretching and follow-up by the therapist.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A system for preventing on the job injuries comprising:
    identifying a company which will benefit from the system and approaching the same with a business proposal;
    evaluating the company's workplace environment by evaluating a personal work environment and an initial physical state of each one of a group of employees employed by the company; wherein the evaluation takes place regardless of whether any injuries have occurred to the employee during the performance of their job; and wherein the initial physical state of each one of the group of employees is evaluated by conducting an ergonomic evaluation and an occupational therapy evaluation of that group of employees;
    assessing data gathered during the ergonomic evaluation and the occupational therapy evaluation;
    developing a corrective therapeutic program to address areas of concern in the initial physical states of one or more of the group of employees, which areas of concern were identified during the assessment;
    implementing the corrective therapeutic program through instruction of each one of the group of employees; and
    conducting periodic follow-up evaluations and adjusting the corrective therapeutic program as required.

2. The system as defined in claim 1, wherein the step of conducting periodic follow-up evaluations is performed until a desired predetermined outcome of the system is reached.

3. The system as defined in claim 2, wherein a first desired outcome is healing of physical deterioration in affected employees identified during the assessment.

4. The system as defined in claim 1, wherein the evaluation step includes:
    identifying a plurality of jobs at the company that involve potentially injurious tasks.

5. The system as defined in claim 4, wherein the evaluation step further includes the steps of:
    conducting the ergonomic evaluation of the personal work environments of a first group of employees who perform an identified first job that involves potentially injurious activities; and
    conducting the occupational therapy evaluation of the first group of employees.

6. The system as defined in claim 5, wherein the step of conducting an ergonomic evaluation of the first group of employees includes:
   observing each of a plurality of individuals in the first group perform the first job,
   recording the observations for each individual onto a set of prepared evaluation forms;
   interviewing each of the individuals in the first group; and
   recording any areas of concern identified by each individual onto the set of evaluation forms for that individual.

7. The system as defined in claim 6, wherein the step of conducting an occupational therapy evaluation of the first group of employees includes:
   conducting a plurality of occupational therapy tests on each of the individuals in the first group to determine a baseline range of motion for each of a plurality of areas of the individuals' bodies that are utilized in the performing of the first job; and
   recording the results of the plurality of occupational therapy tests onto the set of evaluation forms for each of the individuals.

8. The system as defined in claim 7, wherein the step of assessing the results of the ergonomic and occupational therapy evaluations includes:
   compiling the results of each of a plurality of questions on the evaluation forms;
   performing statistical operations on the compiled results for the occupational therapy tests to obtain a combined baseline level of pain in each tested body area and a combined baseline range of motion in each tested body area for all of the individuals in the first group; and
   entering the results of the statistical operations onto a prepared baseline form for use in developing therapies to address a plurality of body areas of concern for the first group.

9. The system as defined in claim 8, wherein the step of assessing the results of the ergonomic and occupational therapy evaluations further includes the step of:
   compiling the recorded ergonomic observations from the evaluation forms for each of the individuals in the first group;
   performing statistical operations on the compiled ergonomic results to obtain a combined ergonomic baseline; and
   entering the results of the statistical operations for the ergonomic results onto the baseline form.

10. The system as defined in claim 9, wherein the step of developing therapies includes the steps of:
   reviewing the baseline form to note one or more of the plurality of body areas of concern identified during the occupational therapy evaluation;
   reviewing a database of stretches;
   selecting a first group of stretches from the database to treat the one or more of the plurality of body areas of concern;
   selecting a second group of stretches from the database to treat the one or more of the plurality of body areas of concern, wherein the second group of stretches are more physically challenging than the first group thereof,
   printing the first group of stretches onto a first sheet of paper; and
   printing the second group of stretches onto a second sheet of paper.

11. The system as defined in claim 10, wherein the step of developing therapies further includes the steps of:
   reviewing the baseline form to note one or more of the plurality of identified ergonomic areas of concern;
   reviewing a database of corrective ergonomic therapies;
   selecting a group of the corrective ergonomic therapies to address the one or more of the plurality of identified ergonomic areas of concern;
   recording the group of corrective ergonomic therapies on a prepared instruction sheet.

12. The system as defined in claim 11, wherein the step of developing therapies further includes the step of:
   compiling the first and second printed sheets of stretches with the instruction sheet to form an instruction program.

13. The system as defined in claim 12, wherein the step of implementing the corrective program includes:
   gathering the first group of employees together;
   discussing the instruction program;
   demonstrating the selected group of corrective ergonomic therapies printed on the instruction sheet;
   demonstrating the first group of stretches printed on the first sheet of paper.

14. The system as defined in claim 13, wherein the step of implementing the corrective program further includes:
   watching the individuals in the first group of employees perform their job utilizing the demonstrated corrective ergonomic therapies;
   watching the individuals in the first group of employees perform the first group of stretches;
   correcting any of the performed ergonomic therapies and first group of stretches.

15. The system as defined in claim 14, wherein the step of following up includes:
   allowing a predetermined period of time to pass;
   conducting a second evaluation and second assessment to determine a combined follow-up physical status for the first group of employees;
   demonstrating the second group of stretches printed on the second sheet of paper;
   watching the individuals of the first group of employees perform the second group of stretches; and
   correcting any of the performed second group of stretches.

16. The system as defined in claim 15, wherein the step of following up further comprising the steps of:
   selecting a third group of stretches from the database of stretches; wherein the third group of stretches is more physically challenging than the second group thereof;
   printing the third group of stretches onto a third sheet of paper;
   demonstrating the third group of stretches to the first group of employees;
   watching the individuals of the first group perform the third group of stretches; and
   correcting any of the performed third group of stretches.

17. The system as defined in claim 13; wherein the step of implementation of the therapeutic program further includes the steps of:
   selecting a volunteer coach from among the individuals of the first group of employees; and
   training the volunteer coach to do the first group of stretches.

18. The system as defined in claim 16, further comprising the steps of:
   conducting an ergonomic evaluation of a second group of employees who perform an identified second job that involves potentially injurious activities;
   conducting an occupational therapy evaluation of the second group of employees; and implementing a second corrective therapeutic program to address a plurality of issues identified during the ergonomic and occupational therapy evaluations of the second group of employees.

19. The system as defined in claim 2, wherein a second desired outcome of the program is reaching a desired threshold of improvement in the physical state of the group of employees.

20. The system as defined in claim 2, wherein a third desired outcome of the program is minimizing injurious activities identified during the evaluation to reduce the possibility of the employees becoming injured during their normal work-related activities.

21. The system as defined in claim 2, wherein a fourth desired outcome of the program is relief of task-generated pain identified by the group of employees during the evaluation.

22. The system as defined in claim 1, further comprising the step of:
    making changes to each employee's personal work environment to address possible causes of future injury to the employee in that environment.

23. The system as defined in claim 1, wherein the steps of evaluating the company's workplace environment, implementing the corrective therapeutic program, conducting periodic follow-up evaluations all take place at the company's workplace.

24. The system as defined in claim 4, wherein the potentially injurious tasks are any frequently repeated physical movements that are required for a worker to perform in order to do their daily work.

25. The system as defined in claim 1, wherein the ergonomic and occupational therapy evaluations further include the steps of:
    observing one or more first physical body movements the employee has to make to perform their job; and
    testing the range of motion the employee's body possesses to make those one or more first physical body movements.

26. The system as defined in claim 25, wherein the step of developing the corrective therapeutic program includes:
    selecting one or more second physical body movements to be practiced by each one of the group of employees in order to counteract the first physical body movements and to improve the range of motion of each one of the group of employees.

27. The system as defined in claim 26, wherein the second physical body movements are selected from a group of physical stretches and exercises.

28. The system as defined in claim 27, wherein the step of implementing the therapeutic program includes the step of teaching the selected group of physical stretches and exercises to the group of employees.

29. The system as defined in claim 28, wherein the step of teaching the selected group of physical stretches and exercises to the group of employees occurs at the company's workplace.

30. The system as defined in claim 1, wherein the step of evaluating the initial physical state of the group of employees is taken before the employees become injured on the job.

31. The system as defined in claim 1, wherein the step of implementing the corrective therapeutic program is taken before the employees become injured on the job.

32. The system as defined in claim 1, wherein the step of teaching the selected group of physical stretches and exercises to the group of employees is taken before the employees become injured on the job.

* * * * *